US00PP09469P

United States Patent [19]

Meilland

[11] Patent Number: Plant 9,469

[45] Date of Patent: Mar. 12, 1996

[54] SHRUB ROSE PLANT NAMED 'MEIBONRIB'

[75] Inventor: Iain A. Meilland, Antibes, France

[73] Assignee: The Conard-Pyle Company, West Grove, Pa.

[21] Appl. No.: 496,160

[22] Filed: Jun. 28, 1995

[51] Int. Cl.[6] ..... A01H 5/00

[52] U.S. Cl. ..... Plt./1

[58] Field of Search ..... Plt./1, 22

*Primary Examiner*—Howard J. Locker

*Attorney, Agent, or Firm*—Burns, Doane, Swecker & Mathis

[57] ABSTRACT

A new and distinct variety of Shrub rose plant is provided which forms on an abundant basis substantially continuously throughout the season attractive long-lasting large double blossoms that are Magenta Pink in coloration. The blossoms are well-formed and are somewhat uniform in appearance. The new variety also forms attractive dark green glossy foliage. The plant possesses a somewhat unusual growth habit that tends to creep along the ground. Also, the new variety exhibits very good disease resistance, and is well suited for growing as ornamentation in the landscape.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) was *Rosa sempervirens*. The male parent (i.e., the pollen parent) of the new variety was the product of the artificial pollination of the 'Delbir' variety (non-patented in the United States) and the 'Meidomonac' variety (U.S. Plant Pat. No. 5,105). The 'Delbir' variety is marketed under the Milrose trademark and the 'Meidomonac' variety is being marketed under the Bonica trademark. The parentage of the new variety can be summarized as follows:

(*Rosa sempervirens*×('Delbir'×'Meidomonac').

The seeds resulting from the above pollination were sown and small plants were obtained which were physically and biologically different from each other. Selective study resulted in the identification of a single plant of the new variety.

It is found that the new variety of Shrub rose plant possesses the following combination of characteristisc:

(a) forms on an abundant basis substantially throughout the season attractive large double blossoms that are Magenta Pink in coloration, (b) forms attractive dark green glossy foliage, (c) creeps as a ground cover and is well suited for growing in the landscape, and (d) exhibits very good disease resistance.

The new variety meets the needs of the horticultural industry and can be grown to particular advantage as an attractive ground cover Shrub rose in parks, gardens, public areas, and residential landscapes.

The new variety of the present invention has been found to undergo asexual propagation by a number of routes in France including budding, grafting and cuttings. Asexual propagation by the above-mentioned routes as performed in France has shown that the characteristics of the new variety are homogeneous and stable and are strictly transmissible from one generation to another.

The new variety has been named the 'Meibonrib' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were three years of age and were observed during September while growing on their own roots outdoors at Le Cannet des Maures, Var, France.

DETAILED DESCRIPTION

Figures 1, 2, 3, 4, 5, 6, 7, 8, 9, 10, 11, 12, 13, 14:
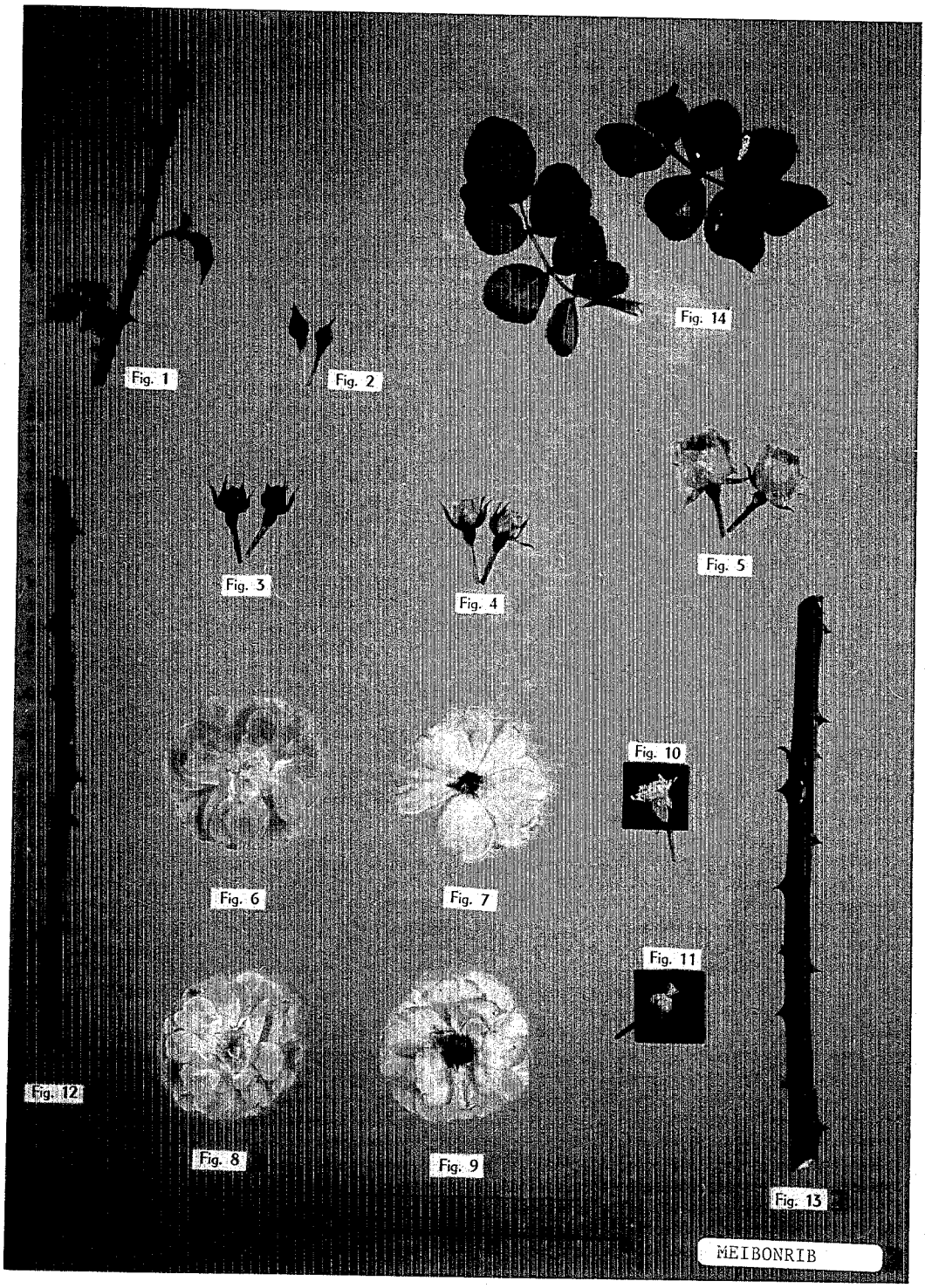
FIG. 1 illustrates a specimen of a young shoot.
FIG. 2 illustrates specimens of two floral buds before the opening of the sepals.
FIG. 3 illustrates specimens of two floral buds as the sepals begin to open.
FIG. 4 illustrates specimens of two floral buds as the petals begin to open.
FIG. 5 illustrate specimens of two flowers in the course of blooming.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of two leaves with seven leaflets each — upper surface (right) and under surface (left).

The chart used in the identification of the colors is that of The Royal Horticultural Society (R.H.S. Colour Chart). The terminology preceding the numbered reference to the chart has been added to indicate in more common terms the corresponding color. The description is based on the observation of three year-old specimens of the new variety while grown outdoors on their own roots during October at Le Cannet des Maures, Var, France.

Class: Shrub.

Plant:

*Height.*—Approximately 120 cm. on average at the end of the growing season.

*Habit.*—Creeps as a ground cover.

Branches:

*Color.*—Young stems: lettuce green, Yellow-Green Group 144B. Adult wood: light green, Yellow-Green Group 146C.

*Thorns.*—Size: medium. Quantity: moderately numerous. Color: reddish-greenish on young stems and pinkish on adult wood.

Leaves:

*Stipules.*—Adnate, pectinate, very wide, dentate, and linear.

Petioles.—Upper surface: striped reddish on young foliage and medium green on adult foliage with more or less glandular edges. Under surface: light green with numerous small thorns.

*Leaflets.*—Number 5 and 7 (most often). Shape: oval. Serration: serrated (as illustrated). Texture: leathery. General appearance: dense and glossy. Color (young foliage): Upper surface: bronze green, Yellow-Green Group 146A. Under surface: medium green, Yellow-Green Group 146B. Color (adult foliage): Upper surface: dark green, Yellow-Green Group 147A. Under surface: medium green, Yellow-Green Group 147B.

Inflorescence:

*Number of flowers.*—Approximately 2 to 7 flowers per stem.

*Peduncle.*—Medium green, more or less tinted with reddish coloration, glandular, and approximately 0.5 cm. in length on average.

*Sepals.*—Upper surface: tomentose, and greenish in coloration. Under surface: light green and more or less tinted with reddish coloration and glandular.

*Buds.*—Shape: globular. Length: approximately 0.5 cm. on average. Size: small. Color when opening: Upper surface: Spinel Pink, Red Group 54B. Under surface: Spinel Pink, Red Group 54B.

*Flower.*—Form: flat-cupped. Diameter: approximately 5 to 6 cm. on average. Color (when opening begins): Upper surface: Spinel Pink, Red Group 54B. Under surface: Spinel Pink, Red Group 54B. Color (when blooming): Upper surface: light Magenta Pink, Red-Purple Group 66C. Under surface: light Magenta Pink, Red-Purple Group 66C. Color (at end of opening): Upper surface: light Roseine Purple, Red-Purple Group 68C. Under surface: medium Roseine Purple, Red-Purple Group 68B. Fragrance: none. Lasting quality: long. Petal form: oval and cordiform. Petal drop: good. Stamen number: approximately 46 on average. Anthers: Normal golden yellow in coloration. Filaments: normal and yellowish in coloration. Pistils: approximately 24 on average. Stigmas: normal and greenish in coloration. Styles: greenish. Receptacle: medium green, more or less tinted with reddish coloration, and in longitudinal section it is in the shape of a pear.

Development:

*Vegetation.*—Vigorous.

*Blooming.*—Abundant and substantially continuous.

*Aptitude to bear fruits.*—Normal.

*Resistance to diseases.*—Very good.

I claim:

1. A new and distinct variety of Shrub rose plant characterized by the following combination of characteristics:

(a) forms on an abundant basis substantially throughout the season attractive large double blossoms that are Magenta Pink in coloration, (b) forms attractive dark green glossy foliage, (c) creeps as a ground cover and is well suited for growing in the landscape, and (d) exhibits very good disease resistance;

substantially as herein shown and described.

* * * * *

MEIBONRIB